United States Patent [19]
Hughes

[11] Patent Number: 4,757,515
[45] Date of Patent: Jul. 12, 1988

[54] LASER TUBE CASING

[75] Inventor: John L. Hughes, Canberra, Australia

[73] Assignee: Hughes Technology Pty Ltd.

[21] Appl. No.: 734,313

[22] Filed: May 14, 1985

[30] Foreign Application Priority Data

May 14, 1984 [AU] Australia .............................. PG4972

[51] Int. Cl.⁴ .......................... H01S 3/00; A61B 17/36
[52] U.S. Cl. .................................. 372/109; 128/303.1;
128/303.14; 128/396; 219/121.6; 372/107
[58] Field of Search ....................... 372/109, 107;
128/303.1, 362, 395, 396, 397, 398, 303.13,
303.14; 219/121.6

[56] References Cited
U.S. PATENT DOCUMENTS

| 3,652,954 | 3/1972 | Snitzer | 372/107 |
| 3,821,510 | 6/1974 | Muncheryan | 128/395 |
| 4,313,093 | 1/1982 | Suenaga et al. | 372/109 |
| 4,357,649 | 11/1982 | LaCroix | 372/109 |

Primary Examiner—James W. Davie
Assistant Examiner—Georgia Y. Epps
Attorney, Agent, or Firm—Cushman, Darby and Cushman

[57] ABSTRACT

A, safe, hand-held laser beam generator, moulded plastic casing containing grooves for accurately aligning said laser beam generator, with cable anchoring means to prevent both the lateral and rotational movement of laser generator. The invention has application in surgery, theraputic treatments, laser pointing and materials processing.

6 Claims, 2 Drawing Sheets

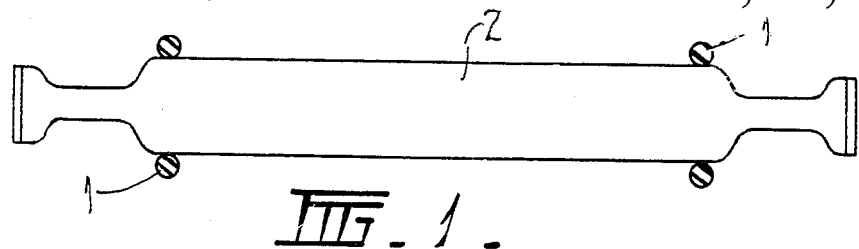
FIG_1_
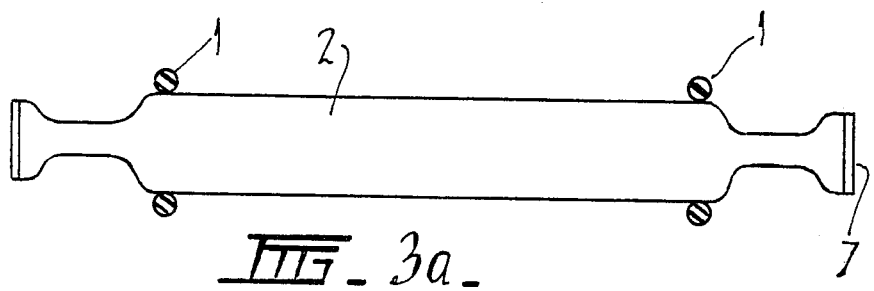
FIG_3a_
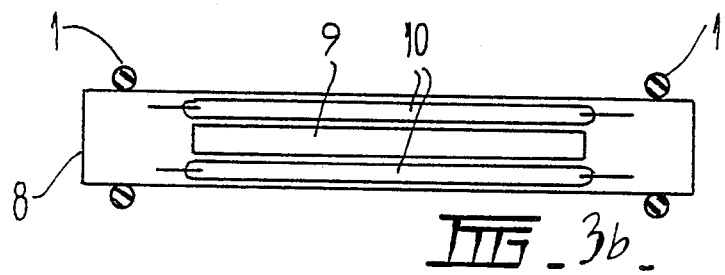
FIG_3b_
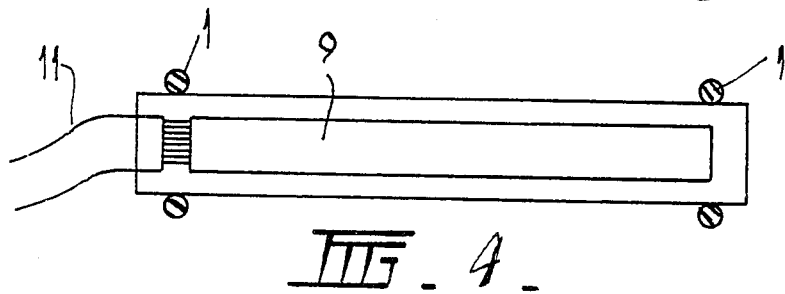
FIG_4_
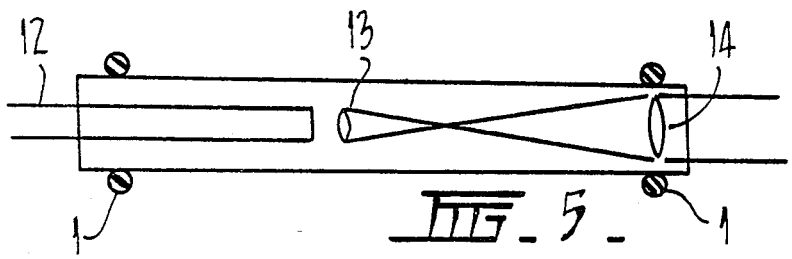
FIG_5_

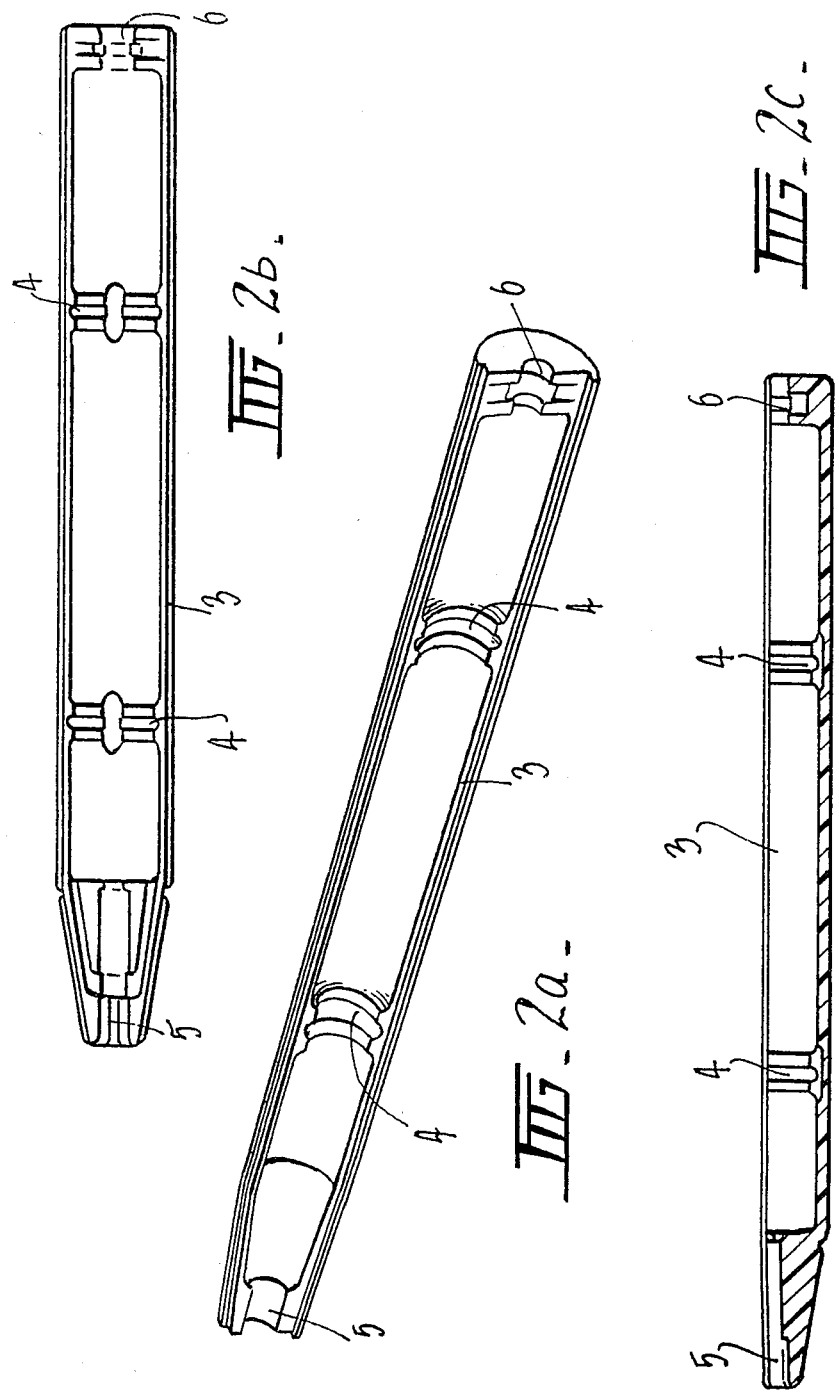

LASER TUBE CASING

FIELD OF THE INVENTION

This invention relates to a mass-produced system for encasing and aligning a laser beam generator, consisting of two identical, injection moulded plastic sections which are glued together after the laser beam generator has been located into one of the plastic sections via "O" ring mountings, the power lead, cooling tubes or optical fibre bundles to said laser beam generator being ringed with a plastic strip which locates into a recess at the rear of each of the plastic sections so that each of the cords have no lateral or rotational movement to upset the alignment of the "O" ring mounted laser beam generator whose alignment within said casing is such as to ensure a clear pathway for the laser beam to emerge through the optical window at the tip of the said casing after the two said casings have been glued together. The invention allows for the rapid assembly of mass-produced laser beam generator systems which are safe to hold in the hand despite the high voltages and heat associated with such laser beam generators whilst at the same time ensuring that there are no relative movements between said casing and said laser beam generator during normal usage, ensuring that the generated laser beam emerges from said casing unimpeded at all times. The invention has application in medical treatments demanding a compact, handheld, powerful laser beam generator, in lecture pointing and in material cutting, welding and workhardening applications.

SUMMARY OF PRIOR ART

Prior art casings for laser beam generators were metallic, bulky and cumbersome to hold in the hand because of the large dimensions of the inefficient prior art laser beam generators and their casings, the hand-held portion of such prior art systems were in the form of the output ends of laser beam delivery systems such as complex articulated arms and fibre optic bundles, said laser beam generators being remote from the hand. With such indirect, hand held laser beam delivery systems, the emerging laser beam was often distorted and reduced to the status of incoherent light due to multiple reflections and scatter either within individual optical fibres or via reflections and misalignment via a multitude of mirrors.

In the present invention, the laser beam is actually generated within hand held system and the laser beam emerges undistorted from said system. As state of the art laser beam generators become more compact, powerful and efficient, the present invention becomes applicable in an increasing range of applications demanding such hand-held laser beam sources.

BACKGROUND OF THE INVENTION

One of the greatest demands made on laser systems is that of the surgeon who requires powerful laser beams to replace surgical knives. The advantage of the laser beam over the knife in surgical applications is well documented, for example, a laser beam is always free of contamination, it coagulates the blood as it cuts and it always remains sharp. However, disadvantages of the laser beam compared to the surgeons knife are the bulkiness of prior art laser beam generators and the extreme safety precautions needed for its operation, ranging from electrical shock hazard to blindness and severe skin burns, particularly in the presence of oxygen.

To approach the effectiveness of a surgeons' knife, the laser beam has to be generated within a compact, hand-held casing, which protects the surgeon from the electrical shock hazards and provides the surgeon with an undistorted, coherent laser beam of appropriate power and wave length.

The present invention provides a suitably compact, hand-held surgeons' laser knife, its plastic casing giving protection against electrical shock hazards and the stable alignment of the laser beam generator to allow for an undistorted laser beam emission.

SUMMARY OF THE INVENTION

It is an object of the present invention to achieve a hand-held laser beam generator unit which generates a powerful, unimpeded laser beam output which is superior to a surgeons' knife.

Another object of the present invention is to allow the mass-production of laser beam generator units by locating the laser beam generator within two "O" rings which in turn are located in grooves within two moulded plastic sections which when glued together form a compact hand-held laser beam generator unit.

A further object for the invention is to provide means of automatically aligning a laser beam generator within its casing so that the laser beam output emerges unimpeded from said casing.

A still further object of the invention is to provide means of locating the leads, tubes or optical fibre bundles to the said laser beam generator such that they do not move laterally or rotate in such a manner as to upset the alignment of said tube.

Another object of the invention is to provide an electrical hazard free casing for said laser beam generator.

The invention allows for the generation of a powerful, hand held laser beam for medical, laser pointing and material processing applications in a safe manner.

The "O" ring locators of the invention can either locate the laser beam generator tube or a tube containing the laser beam generator and its excitation sources. The casing of the laser beam generator can be made water tight and contamination free by sealing its output tip via an optical window or optical lens and sealing the cable into the rear end.

For theraputic applications the invention can provide a direct laser beam output in the focused or unfocused mode. For surgical applications the invention can provide focused beam output over a range of wavelengths ranging up to several kilowatts.

The laser beam generators can take the form of helium-neon tubes, Nd-Yag rods excited either via conventional flashtubes, semiconductor light sources or a combination of both.

The laser beam generators can operate either in the continuous or pulsed modes and in divergent or convergent beams.

Also the laser output beam can be controlled by a foot switch or a fixed timer.

BRIEF DESCRIPTION OF THE DRAWINGS

A better understanding of the invention may be gained from the following description taken in conjunction with the accompanying drawings. It is emphasised that the ensuing teachings are exemplary and not limitative of the scope of the invention.

In the drawings:

FIG. 1 is a schematic layout of a preferred system for the "O" ring mounting of a laser beam generator.

FIGS. 2(a) and 2(b) depict a schematic layout of a preferred system for the injection moulding of one half of the outer casing of said laser beam generator.

FIG. 2(c) is a cross-sectional view of one half of the outer casing of the laser beam generator.

FIG. 3(a) and 3(b) are a schematic layout of the preferred systems for the generation of laser beams in a laser tube containing a gaseous medium, a laser medium container containing a neodymium doped yttrium aluminium garnet laser rod and associated flashtubes for its excitation.

FIG. 4 is a schematic layout of a preferred system for the generation of a laser beam in a neodymium doped yttrium aluminium garnet rod excited via radiation transported via an optical fibre bundle.

FIG. 5 is a schematic layout of a laser beam generator utilizing one end of a composite laser oscillator operating as a phased array transmitter.

DETAILED DESCRIPTION OF THE PREFERRED EMBODIMENT

In FIG. 1 numeral 1 indicates the "O" ring mounting for a laser beam generator as indicated by reference numeral 2.

In FIG. 2(a), reference numeral 3 represents the plastic casing, reference numeral 4 the "O" ring groove, reference numeral 5 the tip of said casing and reference numeral 6 indicates the molded cable locking groove to prevent both the lateral and rotational movement of the laser beam generator. As is shown in FIG. 2a, the tip of the casing has a channel therein for receiving a bundle of optical fibers. In FIG. 2b a different view of one half of the moulded outer casing is shown.

In FIG. 3a reference numeral 2 indicates the laser tube. In FIG. 3b reference numeral 8 indicates a tubular container containing a laser rod indicated by reference numeral 9 which is excited via a flashtube indicated by reference numeral 10.

Laser rod 9 is part of a general laser generator, which, as a person having ordinary skill in the art would know, also includes electrodes and a resonant cavity. The laser generator may be a flash tube actuated neodymium, doped yttrium, aluminum garnet crystal, a helium neon tube, a laser crystal excited via radiation transported from a remotely cited power supply bundle, a phased array composite fiber oscillator or one of other various equivalents known in the art. The structure of the laser generator is such that it is capable of generating one kilowatt of continuous direct beam energy.

In FIG. 4 reference numeral 11 indicates an optical fibre bundle for transporting the excitation radiation in rod 9 to a surgical tool.

In FIG. 5 reference numeral 12 indicates one end of a phased array oscillator whose output is collimated by lenses indicated by reference numerals 13 and 14.

The present invention has applications in surgery, theraputic treatments, laser pointing and laser material processing. A system constructed according to the present invention may further be made watertight by inserting an optical window into the tip opening 5, so that the outer casing thereof can be sterilized without damaging the laser.

I claim:

1. A hand-held portable laser generating system for use in surgical applications comprising
   outer casing means having a first half section and a second half section, each of said first half section and said second half section having a plurality of grooves formed in an interior portion thereof which together form a plurality of annular interior grooves in said outer casing means when said first half section and said second half section are joined together, said first and second half portions of said outer casing means further defining a tip portion having a groove therein through which a bundle of optical fibers may pass;
   means for generating a laser beam disposed within said outer casing means;
   O-ring means positioned in said grooves for surrounding and supporting said generating means, whereby said generating means may be precisely positioned in said outer casing means; and
   means for carrying a laser beam produced by said generating means to a surgical tool, said carrying means being disposed in said groove.

2. A hand-held portable laser generating system according to claim 1, wherein said tip portion is sealed by means of an optical transmitting window, whereby said outer casing may be sterilized without damaging said generating means.

3. A hand-held portable laser generating system according to claim 1 wherein said generating means comprises a helium neon tube.

4. A hand-held portable laser generating system according to claim 1 wherein said generating means is a flash tube excited neodymium, doped yttrium, aluminum garnet crystal.

5. A hand-held portable laser generating system according to claim 1 wherein said generating means comprises a laser crystal excited via radiation transported from a remotely sited power supply via an optical fiber bundle.

6. A hand-held portable laser generating system according to claim 1 wherein said generating means comprises the output end of a phased array composite fiber oscillator.

* * * * *